United States Patent [19]

Parsons et al.

[11] 4,424,058

[45] Jan. 3, 1984

[54] DRAINAGE CONTROL METHOD AND APPARATUS

[76] Inventors: Robert L. Parsons, 1368 Windsong Rd., Orlando, Fla. 32809; Joseph M. Valdespino, 5023 Gold Club Pkwy., Orlando, Fla. 32808; Alan R. Varraux, 5433 Hansel St., Orlando, Fla. 32809; Allen K. Holcomb, 200 W. Gore St., Orlando, Fla. 32806; William M. Hobby, III, 244 Sylvan Blvd., Winter Park, Fla. 32789

[21] Appl. No.: 323,957

[22] Filed: Nov. 23, 1981

[51] Int. Cl.³ .............................................. A61M 27/00
[52] U.S. Cl. ................................... 604/118; 604/129; 604/247; 137/217
[58] Field of Search ................. 128/1 R; 604/10, 118, 604/119, 121, 128, 129, 247; 137/143, 145, 151, 216, 217, 218

[56] References Cited

U.S. PATENT DOCUMENTS

| | | | |
|---|---|---|---|
| 1,782,367 | 11/1930 | Ridgway | 137/218 |
| 2,242,401 | 5/1941 | Loughridge | 137/151 X |
| 3,171,423 | 3/1965 | Dillon | 137/218 |
| 3,730,209 | 5/1973 | Binard et al. | 137/217 |
| 3,954,223 | 5/1976 | Wichman et al. | 137/218 X |
| 4,084,593 | 4/1978 | Jarund | 128/DIG. 25 |

Primary Examiner—Dalton L. Truluck
Attorney, Agent, or Firm—Willaim M. Hobby

[57] ABSTRACT

A drainage control valve apparatus utilizes a pressure relief valve for opening upon a predetermined fluid pressure being applied thereto and a liquid column is used for holding the pressure relief valve open by the weight of the liquid column escaping past the pressure relief valve to apply a negative pressure to the back of a pressure relief valve element. A small opening or a check valve releases the suction column when drainage is complete to allow the pressure relief valve to close. The pressure relief valve may be a spring biased valve and may be adjusted by varying the compression on the spring. The unit may be attached to a patient's leg with a strap. A method of draining a bladder is provided having the steps of opening a pressure relief valve under bladder pressure in a catheter, holding the pressure relief valve open with the suction of a column of liquid formed by the liquid passing the opened pressure relief valve and releasing the pressure relief valve when drainage is substantially complete.

30 Claims, 9 Drawing Figures

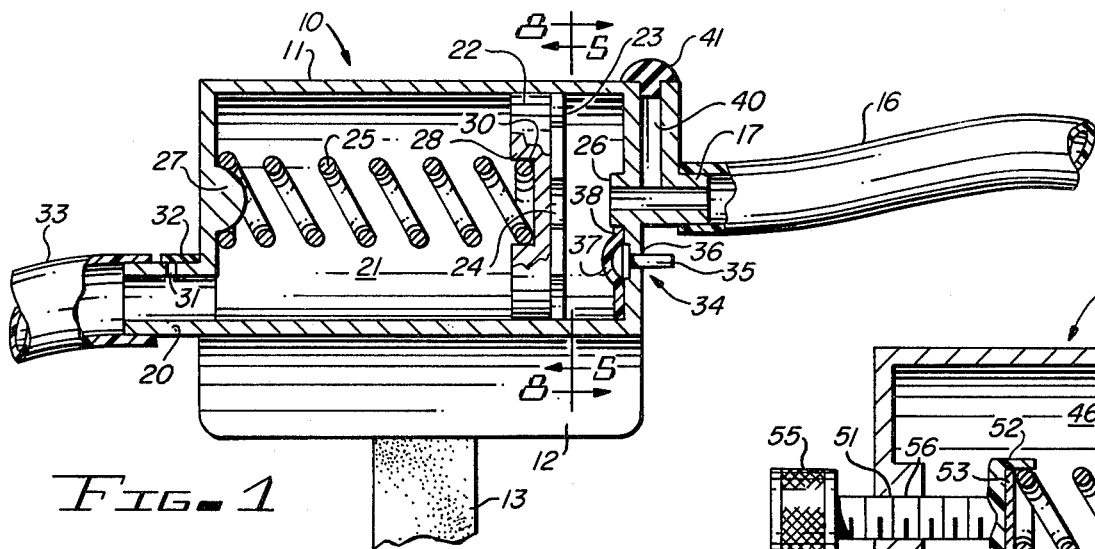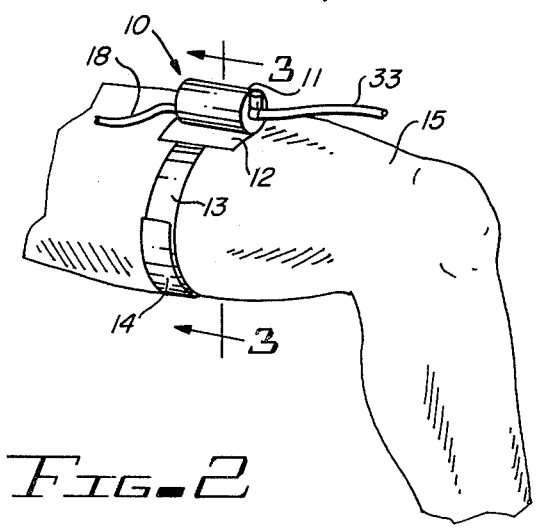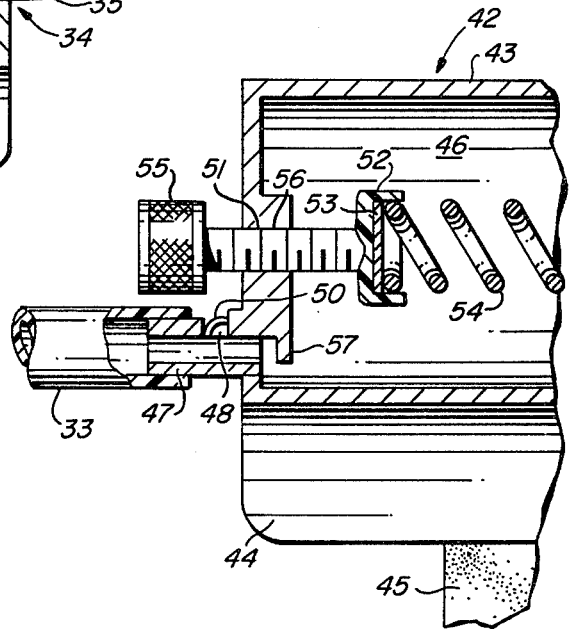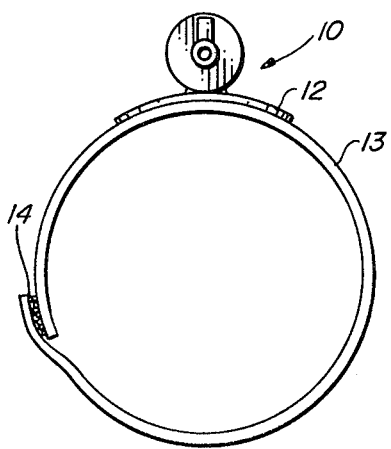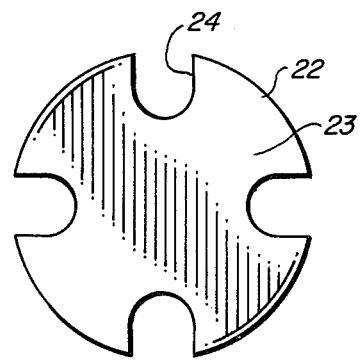

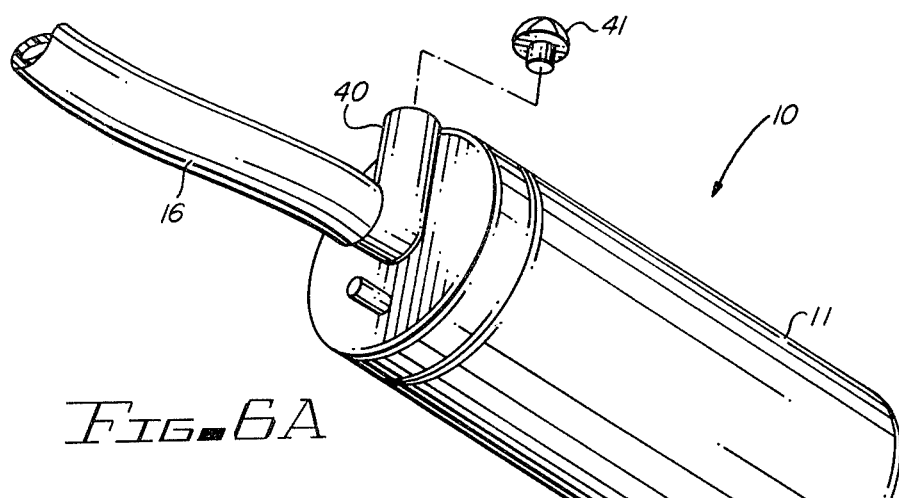
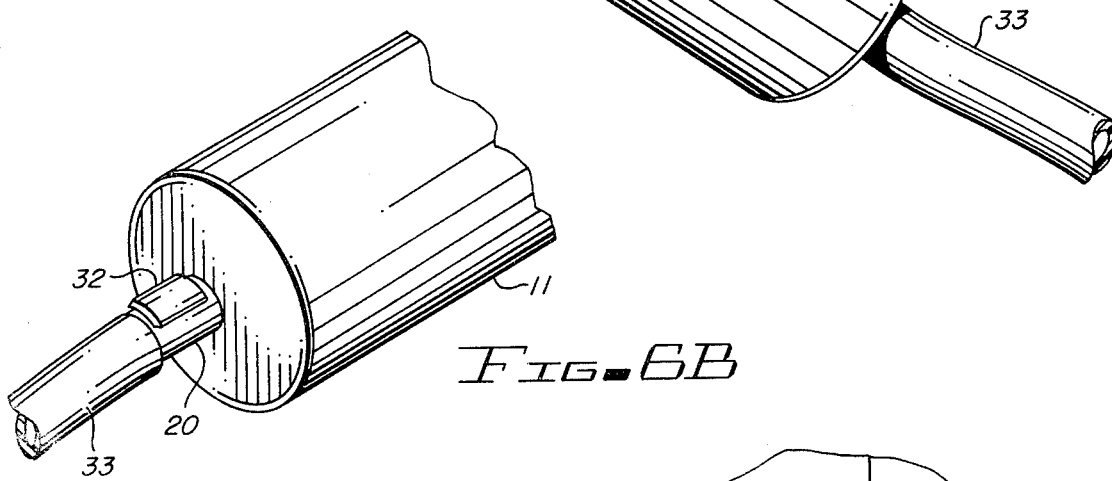
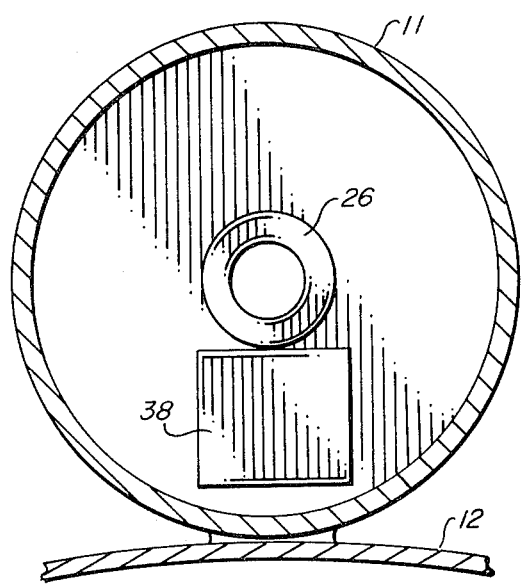
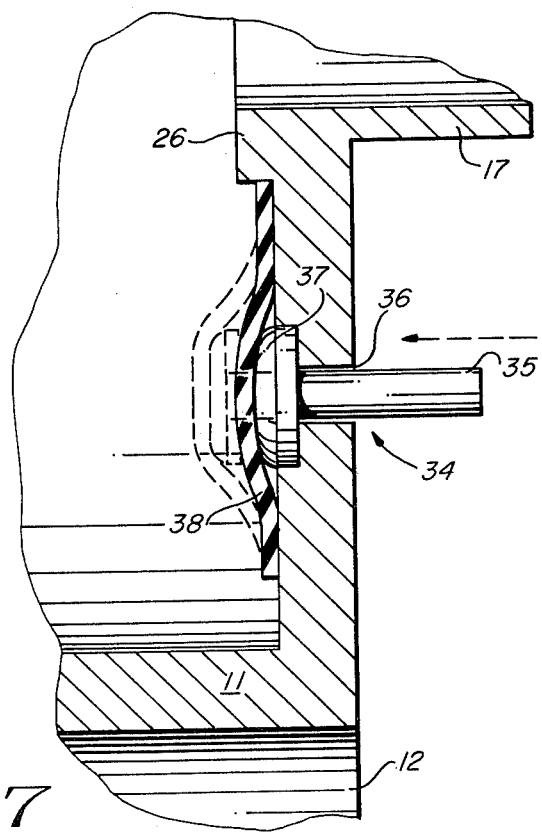

DRAINAGE CONTROL METHOD AND APPARATUS

BACKGROUND OF THE INVENTION

The present invention relates to a drainage control method and valve especially adapted for use with drainage catheters to dump the contents of a bladder upon a predetermined pressure being reached in the valve and to close the valve once the contents has been released into a drainage bag.

Heretofore, it has been a common hospital procedure to obtain continuous drainage of urine from the urinary bladder by means of a catheter passed transurethrally and retained in the bladder by a number of standard and conventional devices. It is usual practice to attach a relative large bore, plastic drainage tube to the distal proximal end of the urinary catheter and lead this drainage tubing along a downhill path over the side of the bed into a collection bottle or bag which is placed below the level of the urinary bladder. Such an apparatus when functioning properly creates a syphon effect in the catheter only to the level of the connection between the catheter and the drainage tube. However, a syphon effect is not obtained in the drainage tube as the bore of the latter is large enough so that air bubbles pass up the drainage tube preventing a syphon action therein. With this arrangement, generally continuous drainage is obtained in that the bladder is always kept empty, there being no provision for automatic and periodic filling and emptying of the bladder.

There are two basic objections to this system. First, the urinary bladder is a hollow distensible organ which depends upon alternate filling and emptying to maintain the tone of its muscular walls. Also, periodic filling and emptying of the bladder is one of the major methods or mechanisms by which the concentration of bacteria in the bladder is kept at low levels. This mechanism depends on dilution of the bacteria which may be existing in the bladder with sterile urine from the ureters followed by periodic and complete emptying of the bladder. It has been demonstrated that if bacteria are introduced into a normal bladder in large concentrations, the bladder is capable of clearing these organisms by this mechanism within approximately 24 to 48 hours. If the bladder is kept from emptying completely, although still allowed to expel portions of its contents periodically or continually, the growth of bacteria in the bladder may be of such magnitude that infection will ensue.

The second objection to the aforementioned conventional method is that most of the catheters used as indwelling bladder catheters do not conform to the contracted shape of the bladder so that "foley tip necrosis" of the dome of the bladder, a syndrome well known to urologists and pathologists, may result. It is felt by some that this pressure ischemic ulcer of the dome of the bladder is the portal by which bacteria enter to infect the bladder. Such infections, common in patients with indwelling catheters, are caused when the dome of the bladder collapses and falls or is drawn down over the indwelling catheter, particularly over the tip of the catheter.

There are several pitfalls in the use of the aforementioned conventional drainage system which are very commonly encountered in hospitals and which accentuate this situation. For example, the drainage tube may be placed below the surface level of urine in the collection bottle or bag. Under these circumstances, the drainage tubing may fill with urine and exert a strong and continuous syphon action in the bladder. This draws the dome of the bladder down over the indwelling catheter and over the tip thereof very much enhancing the formation of pressure ulcers in the dome of the bladder. Also, it has been demonstrated many times that submerging the end of the drainage tube in the urine will allow bacteria to swim up the slowly draining fluid in the drainage or connecting tubing and infect the bladder by that route.

Another pitfall of the aforesaid conventional drainage system is that if the drainage tubing is not led straight from the indwelling catheter to the collection bottle, urine will collect to form pockets in any loops which may be in the tubing thereby causing a back pressure in the bladder with a resulting residual stagnant pool of urine therein. Such residual pooling is well known to hasten the onset of infection.

It is an advantage of the present invention to avoid the aforesaid difficulties of known prior art practices by providing a method and apparatus for drainage of fluids from the body with an indwelling bladder catheter, or the like, which automatically and periodically collapses and drains the cavity insuring its complete emptying and which then allows the cavity to distend and collect the fluid once again to a predetermined pressure before recycling, while essentially emptying and clearing the drainage tubing of fluid at the end of each cycle.

In the past, various attempts have been made to provide a drainage system for the drainage of urine from the urinary bladder to overcome the objections to a conventional drainage catheter. In U.S. Pat. Nos. 2,602,448 and 2,860,636, a title drainage and irrigating unit utilizes a syphon in combination with a reservoir to provide cycle draining of the bladder. However, this system like other syphon systems, requires that a loop be fed at a predetermined height above the patient's bladder to create two syphon legs which will create the pressure at which the syphon will empty the bladder. Pressure release is controlled by raising the height of the device on a bedside tree and is very precise and subject to variations by a shifting patient and prevents the patient from moving around while the catheter is in place.

In U.S. Pat. No. 3,598,124, the syphon leg is controlled by merely attaching the catheter to a bedside tree at predetermined adjusted height, which varies the pressure at which the bladder will drain and providing a flutter valve near the patient to break the syphon action of the system once the bladder has drained. In U.S. Pat. No. 4,230,102, a device for the draining of a urine bladder is shown in which a T-joint has been placed on a catheter and has a pressure membrane attached thereto in a large casing for actuating a pressure switch which in turn actuates an electric motor driving a gear train and cam. A cam follow is spring loaded to clamp the catheter for two minute cycles upon actuation by the pressure switch to drain the bladder. This type of device, however, is expensive and bulky and positions an electrical apparatus adjacent the catheter. In U.S. Pat. No. 3,768,102, an implantable artificial urethal valve is shown; while in U.S. Pat. No. 3,642,004 a urethal valve having an electrically actuated solenoid in the tip thereof is shown. In U.S. Pat. No. 3,419,009, another vented surgical drainage tube is an automatic regulating device for bladder irrigation devices utilizing an electrical control system with a timing cam.

The present invention is directed towards a simplified device to control the drainage of the bladder irrespective of a patient's position and allows the patient mobility while the catheter is attached. The present invention is designed to be a single patient device which is sufficiently inexpensive to be thrown away after use by the patient.

SUMMARY OF THE INVENTION

A draining control valve apparatus is provided having a pressure relief valve for opening upon a predetermined fluid pressure being applied thereto and a suction column for holding the pressure relief valve open by the weight of a liquid column escaping past the pressure relief valve. The drainage control valve may include a housing having an inlet having a tube attached thereto and an outlet having an outlet tube attached thereto. The inlet tube can be connected to a urinary bladder, while the outlet tube can be connected to a drainage bag. A valve element located in the housing is biased against a valve seat to open upon a predetermined pressure thereagainst by liquid in the housing inlet. An outlet column is formed by the outlet and tube attached thereto to create a suction with a liquid column formed from the liquid passing by the valve element to place a suction on the back of the valve element to open the valve element and to hold the valve element open until the drainage is complete. The column suction relief opening relieves the negative pressure on the back of the valve element, thereby allowing the valve element to close. The suction relief can be either a small opening of predetermined size in the outlet or the outlet tube which may be covered with a filter, or may be a small check valve. The valve element may be a spring biased piston held in position within the housing and may have a compression adjusting member to vary the pressure at which the pressure relief valve will open. The drainage control valve may be provided with an arcuate base and a flexible strap for attaching to a patient's leg. A manual valve release allows the valve to be manually actuated prior to it reaching the predetermined pressure required to automatically actuate the valve.

A method of draining the bladder has the steps of opening a pressure relief valve with the bladder pressure in a catheter, holding the pressure relief valve open with the suction of a column of liquid formed by liquid passing the pressure relief valve and releasing the pressure relief valve when drainage is substantially complete.

BRIEF DESCRIPTION OF THE DRAWINGS

Other objects, features and advantages of the present invention will be apparent from the written description and the drawings, in which:

FIG. 1 is a sectional view of a preferred embodiment of the present invention;

FIG. 2 is a perspective view of a drainage control valve in accordance with the present invention attached to a patient's leg;

FIG. 3 is a sectional view taken on the line 3—3 of FIG. 2;

FIG. 4 is a sectional view of an alternate embodiment of a drainage control valve in accordance with the present invention;

FIG. 5 is a sectional view taken on the line 5—5 of FIG. 1;

FIG. 6A is a bottom perspective view of a drainage control valve in accordance with the present invention;

FIG. 6B is a cutaway top perspective view of the valve of FIG. 6A;

FIG. 7 is a partial sectional view showing the manual valve actuation portion on an enlarged scale; and FIG. 8 is a sectional view taken on the line 8—8 of FIG. 1.

DESCRIPTION OF THE PREFERRED EMBODIMENTS

Referring to FIGS. 1 through 3 and 5 through 7, a drainage control valve 10 is shown having a cylindrical housing 11 with an arcuate base plate 12 which may be of a flexible polymer material having a flexible strap 13 attached thereto, along with a hook and loop fastener 14 for attaching the strap and the drainage control valve 10 to a patient's leg 15. A drainage catheter 16 may be connected to a patient's bladder and to an inlet 17 on the valve 10, while a drainage tube 18 is connected onto an outlet 20 of the valve 10 and to a drainage bag which may be located beside a bed or which may be attached to the bottom of a patient's leg. The valve has a chamber 21 having a valve element or piston 22 slidably positioned in the chamber 22 to slide along the interior walls thereof. The piston 22 has a valve seal 23 which may be made of a soft rubber, or the like, attached to one side thereof and may have a plurality of slots 24 as more clearly shown in FIG. 5. The sliding valve element 22 is spring biased with a spring 25 which may be a small stainless steel helical spring compressed to drive the valve element 22 against the valve seat 26 adjacent the inside of the inlet 17 to seal the inlet against the valve seat 26. The spring 25 is held in position by a supporting protruding surface 27 which protrudes into the base of the spring. It will, of course, be clear that a cylindrical spring support could extend to the outside of the spring if desired. The opposite end of the spring 28 is supported in the piston 22 by a cylindrical removed area 30 therein. The outlet 20 has a small opening 31 covered by a filter 32 on the outlet 20 inside of the tube 33. As a patient's bladder fills and the pressure increases in the drainage catheter tube portion 16 and the inlet 17 of the valve 10, pressure is applied against a small portion of the surface of the valve element 22 until the pressure overcomes the bias of the spring 25. At this time, the piston 22 is slid only slightly to allow small amounts of fluid to drip through the valve around the notches 24 and into the chamber 21. A small amount of flow feeds into the outlet and tubes 33 towards a drainage bag which is generally located on the side of the bed.

As the urine accumulates in the tube 33, it forms a suction column and the weight of the column places a suction on the chamber 21 and against the back surface of the piston 22 which pulls the piston open further and allows the urine from the bladder to substantially empty through the tube 16, inlet 17, through the valve 10 and into the drainage bag. As the bladder is draining through the tube 33 and through the outlet 22, small amounts of air are pulled through the opening 31 and through the filter 32, which is carried with the urine into the drainage bag. However, once the urine ceases to flow, air will leak through the opening 31 to relieve the suction or negative pressure in the chamber 21 being applied against the back of the valve element 22 to thereby allow the back of the valve element 22 to close against the valve seal 26 to again seal the valve until sufficient pressure builds up in the bladder to again actuate the valve 10.

The suction column also helps more fully drain the bladder similar to a syphon device, but may not be a true syphon which normally has a short leg and a long leg and is actuated by the suction created by the fluid column in the long leg. However, depending upon the position of the patient, there may not be a short leg in the present invention. A manual release 34 has a release stem 35 passing through an opening 36 and connected to a head 37 to allow a patient to push the relief stem 35 to push against a flexible elastomer or rubber surface 38 and against the top of the valve element 22 to open the valve manually. The flexible elastomer material 38 prevents any contact in the valve with the atmosphere and also acts as a spring to return the stem 35 when released. An alternate opening 40 has a rubber cover or cap 41 sealing the opening in a manner to allow a needle to be inserted through the rubber sealed cap 41 for feeding a solution into the patient's bladder. Advantageously, if too much solution is fed to the bladder, the valve 10 will actuate and drain the bladder. The drainage control unit capped opening in the proximal housing allows bladder medication to be inserted through this opening and periodically emptied by the action of the valve. Antimicrobial solutions and antispasmotic medications may be used in the bladder this way.

In FIG. 3, the valve 10 is seen attached to the plate 12 and to the strap 13 and having a hook and loop fastener for attaching the strap to different size legs of patients. It will, of course, be clear that the present valve 10 can operate without the strap 13 by just laying the valve 10 on the bed beside the patient or even beside the bed and will not be actuated in any event until sufficient pressure from the bladder is applied against the valve element 22.

Turning now to FIG. 4, a slightly modified embodiment has a drainage valve 42 having a housing 43 and an arcuate leg conforming mount 44 connected to a strap 45. The housing 43 has chamber 46 therein similar to the embodiment of FIG. 1. This embodiment differs in that the drainage tube 33 is connected to an outlet 47 and has a small check valve 48 which may be a small rubber flap for closing the surface against the escapement of air or liquid, but to allow air to be sucked in with the flow of liquid and to break the suction created in the chamber 46 to release the valve element. This embodiment also has a filter 50 covering the opening. The embodiment of FIG. 4 also differs in that it has a threaded spring support member 51 having a small spring supporting cup 52 mounted on one end having a slip washer, such as a teflon washer 53, therein supported against a spring 54. A small knurled handle 55 is attached to the other end of the threaded shaft 51 and threaded through a threaded opening 56 in the housing 43, Rotating the knob 55 will thread the threaded shaft 51 into or out of the housing 43, increasing or reducing the compression of the spring 54. The spring slides on a slip washer 53 thereby preventing binding of the spring while making adjustments. This embodiment allows the pressure by which the valve 42 is open to be varied in accordance with the patient's requirements; while the embodiments of FIG. 1 may be made in several different sizes requiring a different spring 25 in size for different patients. The ability to vary the opening pre-sure of the drainage control valve permits the apparatus to increase bladder capacity. When used with contracted or small bladders, the opening pressure of the device may be increased at desired increments. This will dilate and distend the bladder to an accepted capacity.

The shaft 51 and knurled knob 55 may be provided with indicia to indicate a particular pressure of any particular setting and may be provided with a click setting for locking the pressure in any particular position as desired without departing from the spirit and scope of the invention. The embodiment of FIG. 4 also has a protruding wall 57 forcing the liquid to follow a circuitous path from the chamber 46 into the tube 33. If a large drainage tube 33 is utilized, a liquid path such as formed by the wall 57 in the offset outlet 47 assist in creating a suction column in the outlet 47 in the tube 33. It has, however, been found that with the small drainage tubes normally used, a suction column will start without a particular sloped passageway to assure the column is completely filled up. This circuitous path can be extended to form other bends or even a knot in the tube 33 to assure that the tube fills at some point, if desired. However, in the case as shown in FIGS. 1 through 3, the catheter rises over the patient's leg and down again, assuring the creation of a suction column even with a larger drainage tube.

It should be clear at this point that a drainage control valve may be inexpensively manufactured for use as a disposable item and is actuated by pressure on the one hand, but is drained by a liquid suction column holding the valve open; but which the suction is relieved upon the completion of the drainage. It should also be clear, however, that the large size of the back of the piston area 22 allows the valve element 22 to be easily held open by the negative pressure against the spring 25 and the size of the chamber 21 which is normally filled with air is under a negative pressure drainage and allows enough compression and expansion to reduce the suction placed on the bladder when the drainage is complete, while the air opening 31 releases the suction in the chamber 21 as soon as the last liquid is passed through the outlet 20. It is anticipated that the housing and valve element can be made of polymer materials by injection molding, or the like, while the spring 25 can be a stainless steel compression spring and other inexpensive materials can be utilized for the seal cover 41 and the elastic member 38. Accordingly, the present invention is not to be construed as limited to the forms shown, which are to be considered illustrative rather than restrictive.

We claim:

1. A drainage control valve for use in the drainage of a bladder comprising in combination:

a housing;

pressure relief valve means located in said housing for opening upon a predetermined fluid pressure being applied thereto and including a valve element movably mounted therein;

suction means for holding said valve element open by the weight of a liquid column escaping past said pressure relieve valve means; and said housing having an offset outlet passageway whereby a suction column is formed when said pressure relief valve means opens to allow the passage of a liquid therethrough.

2. A drainage control valve in accordance with claim 1, in which said valve element is a sliding piston spring biased against a valve seat.

3. A drainage control valve in accordance with claim 2, in which said valve element has a resilient surface on one side thereof for sealing against said valve seat.

4. A drainage control valve in accordance with claim 3, in which said housing has an inlet through said valve seat and an outlet therefrom connected to a drainage tube.

5. A drainage control valve in accorance with claim 1, in which said drainage control valve is provided with a small opening to relieve said suction means for holding said pressure relief means open after substantial drainage of liquid has passed through said drainage control valve.

6. A drainage control valve in accordance with claim 2, in which said housing has a spring positioning portion thereinside for supporting said spring in a predetermined position therein.

7. A drainage control valve in accordance with claim 6, in which said valve element has a spring support portion thereon for supporting said spring on said movable valve element.

8. A drainage control valve in accordance with claim 2, in which said spring is a stainless steel helical compression spring supported in a cylindrical housing of said drainage control valve.

9. A drainage control valve in accordance with claim 1, in which said valve element has means for liquid to pass thereby when said valve element is open.

10. A drainage control valve in accordance with claim 9, in which said valve element is a disc shaped piston having slots formed in the perimeter thereof.

11. A drainage control valve in accordance with claim 1, in which said housing has a release stem passing therethrough for applying pressure against said pressure relief valve means for manually actuating said valve element.

12. A drainage control valve in accordance with claim 11, in which said release stem presses against a flexible elastic surface attached to the inside of said drainage control valve housing, thereby preventing atmospheric air from entering the housing and returning said valve stem following actuation of said valve.

13. A drainage control valve in accordance with claim 12, in which said valve stem has a surface attached thereto on the inside of said housing preventing said valve stem from coming out of the opening in said housing.

14. A drainage control valve in accordance with claim 1, in which said drainage control valve housing is attached to an arcuate mount having a flexible strap attached thereto for attaching said drainage control valve to a patient's leg.

15. A drainage control valve in accordance with claim 14, in which said flexible strap has a hook and loop fastener attached thereto for attaching said drainage control valve to a patient's leg.

16. A drainage control valve in accordance with claim 14, in which said outlet to said drainage control valve is located on the bottom of said cylindrical housing adjacent its arcuate mount and has a suction relief opening therein.

17. A drainage control valve in accordance with claim 16, in which said suction relief opening has a check valve therein to prevent the escape of fluid while allowing air to be sucked into said drainage control valve.

18. A drainage control valve in accordance with claim 1, in which said pressure relief valve means includes a valve element adjustedly biased for opening upon a predetermined fluid pressure as determined by the adjustment of the bias against the valve element.

19. A drainage control valve in accordance with claim 18, in which a threaded shaft passes through one end of the housing of said drainage control valve and has a surface connected to a helical spring biasing said valve element, whereby threading said threaded shaft into and out of said housing will vary the compression on said spring against said valve element to vary the pressure for the opening of said pressure relief valve means.

20. A drainage control valve in accordance with claim 19, in which said threaded shaft has a handle on one end.

21. A drainage control valve in accordance with claim 20, in which said threaded shaft spring support surface has a slip washer therein to prevent the binding of said compression spring.

22. A drainage control valve in accordance with claim 1, in which said valve element is a disc having sufficient thickness to prevent said disc from cocking while sliding along the inner surface of the housing of said drainage control valve.

23. A drainage control valve in accordance with claim 1, in which said valve element has an opening therethrough to allow the passage of liquid.

24. A drainage control valve in accordance with claim 1, in which said valve element has a surface sized to reduce the suction required to open said valve element with said suction means.

25. A drainage control valve in accordance with claim 5, in which said drainage control valve opening to relieve said suction means has a filter mounted to cover said opening in said housing.

26. A drainage control valve in accordance with claim 1, in which said housing has a capped opening therein for inserting a needle for directing a liquid into said bladder.

27. A drainage control valve for the cylindrical drainage of a bladder comprising in combination:
a housing having an inlet, having an inlet tube attached thereto and an outlet having an outlet tube attached thereto;
a valve element located in said housing, said valve element being biased to open upon a predetermined pressure being reached by liquid in said housing inlet;
an outlet column formed by said tube attached to said housing outlet to create a suction with a liquid column formed by the liquid passing by said valve element to hold said valve element open by the suction on the back of said valve element until substantial draining is complete; and
column suction relief means to relieve the negative pressure on said valve element and thereby allow said valve element to close.

28. A drainage control valve in accordance with claim 27, having a valve element of enlarged size relative to said outlet tube to thereby increase the pressure holding said valve element open by the suction of said liquid column in said outlet tube.

29. A drainage control valve in accordance with claim 27, in which said valve element has adjustable biasing means biasing said valve element to open upon a predetermined pressure, which predetermined pressure is variable with said adjustable biasing means.

30. A drainage control valve in accordance with claim 27, in which said housing has a capped opening therein for inserting a needle for directing a liquid into said bladder.

* * * * *